United States Patent [19]
Ahlquist et al.

[11] Patent Number: 5,466,788
[45] Date of Patent: Nov. 14, 1995

[54] SUBGENOMIC PROMOTER

[75] Inventors: Paul G. Ahlquist, Madison, Wis.; Roy C. French, Lincoln, Nebr.

[73] Assignee: Mycogen Plant Science, Inc., San Diego, Calif.

[21] Appl. No.: 296,080

[22] Filed: Aug. 25, 1994

Related U.S. Application Data

[63] Continuation of Ser. No. 197,222, Feb. 16, 1994, abandoned, which is a continuation of Ser. No. 69,457, Jun. 1, 1993, abandoned, which is a continuation of Ser. No. 683,516, Apr. 8, 1991, abandoned, which is a continuation of Ser. No. 168,691, Mar. 16, 1988, abandoned, and a continuation-in-part of Ser. No. 368,939, Jun. 19, 1989, abandoned, which is a continuation of Ser. No. 709,181, Mar. 7, 1985, abandoned.

[51] Int. Cl.$^6$ .............................. C12N 15/11; C12N 15/82
[52] U.S. Cl. ...................... 536/24.1; 536/23.1; 435/172.3
[58] Field of Search ............................ 435/172.1, 172.3; 536/23.1, 24.1; 935/34, 35

[56] References Cited

U.S. PATENT DOCUMENTS 4,820,639  4/1989  Gehrke ...................................... 435/68

OTHER PUBLICATIONS

Gallie et al. (1987) Nucleic Acid Research, vol. 15 #21 pp. 8693–8711.
Vloten–Dating et al. (1985) Plant Molecular Biology 4:pp. 323–326.
French and Ahlquist (1987) J. Virol. 61:1457–1465.
Ahlquist, P. and French, R. (1988) in RNA Genetics Book 2: RNA Variability, Chapter 3, Domingo et al. (eds.) CRC Press, Orlando, Fla.
French, R. et al. (1986) Science 231:1294–1297.
Ahlquist, P. et al. (1981) J. Mol. Biol. 153:23–38.
Miller, W. et al. (1985) Nature 313:68–70.
Marsh, L. et al. (1987) in Positive Strand RNA Viruses, A. R. Liss, Inc. (ed.) New York, pp. 327–336.
Ou, J.–H. et al. (1982) Proc. Natl. Acad. Sci. USA 79:5235–5239.
Barker, R. et al. (1983) Nucl. Acids Res. 11:2881–2891.
Janda, M. et al. (1987) Virology 158:259–262.
Ahlquist, P. and Janda, M. (1984) Mol. Cell. Biol. 4:2876–2882.
Takamatsu, et al. (1987) The EMBO Journal vol. 6 No. 2 pp. 307–311.
Ahlquist et al. (1985) Journal of Virology, vol. 53, No. 2 pp. 536–542.
"Gene Science" van Nostrand's Scientific Encyclopedia, 7th Ed. (D. M. Considine and G. D. Considine, eds.) I:1302–1309 (1989).

*Primary Examiner*—Gary Benzion
*Attorney, Agent, or Firm*—Saliwanchik & Saliwanchik

[57] ABSTRACT

A subgenomic promoter of a positive strand RNA virus is disclosed which directs the amplified expression of a structural gene in plant tissue. The core region and an upstream activating domain of the subgenomic promoter are identified. This promoter can be utilized in a modified virus, or in an appropriate engineered recombinant DNA derivative, which may be chromosomally integrated or maintained as an episome in transformed cells.

7 Claims, 8 Drawing Sheets

AvaI
CUCGGGGGAGGUUAUCCAUGUUUGUGGAUAUUCUAUGUUGUGUG

Bgl2                                              Sal1
UCUGAGUUAUUAUUAAAAAAAAAAAAAAAAAAAGAUCUAUGUCCUAAUUCAGC GUAUUAAUAAUGUCGAC...

RNA4:    m7GpppGUAUUAAUAAUGUCGAC...

SUBGENOMIC PROMOTER

This is a continuation of application Ser. No. 08/197,222, filed Feb. 16, 1994, now abandoned, which is continuation of application Ser. No. 08/069,457, filed Jun. 1, 1993, now abandoned, which is a continuation of application Ser. No. 07/683,516, filed Apr. 8, 1991, now abandoned, which is a continuation of application Ser. No. 07/168,691, filed Mar. 16, 1988, now abandoned, and a continuation-in-part of Ser. No. 07/368,939, filed Jun. 19, 1989, now abandoned, which is continuation of Ser. No. 06/709,181, filed Mar. 7, 1985, now abandoned.

FIELD OF THE INVENTION

The field of this invention is the area of molecular biology, and it relates in particular to the field of (+) strand RNA viruses. The teachings of the present invention will enable the use of a viral control sequence, termed a subgenomic promoter, for directed gene expression in the appropriate cell host. Specifically, the subgenomic promoter of RNA3 of brome mosaic virus is exemplified to amplify the expression of a structural gene in plant tissue.

BACKGROUND OF THE INVENTION

Single-stranded RNA viruses which are capable of replicating in the cytoplasm of host cells are widespread in nature. Those single-stranded viruses with message-sense genomic RNA molecules are called (+) strand, or positive strand, RNA viruses. Among the known (+) strand RNA viruses there are bacteria-specific, animal-specific, and plant-specific varieties. There is much diversity in the morphology of virus particles, coat proteins, genetic organization, and genome size. The (+) strand RNA viruses include, but are not limited to, Q-beta bacteriophage, poliovirus and alphaviruses (including Sindbis virus) of animal cells, and the bromoviruses (including brome mosaic virus) and the comoviruses (including cucumber mosaic virus) of plants.

A general review of (+) strand virus replication has been published (E. Strauss and J. Strauss (1983) Curr. Top. Microbiol. Immunol. 105:1). A brief summary of the steps follows. Virally determined proteins may be required together with the genomic RNA(S) for infection to occur, or all the viral proteins required to initiate virus replication may be synthesized using the incoming viral genomic RNA as message. There is no DNA intermediate in the replication of the nucleic acid of these viruses; the replication of the genetic information of a (+) strand RNA virus requires the RNA-dependent RNA synthetic capability of cells infected with such viruses. The incoming genomic (+) strand serves as template for the synthesis of (−) strand molecules, and then progeny (+) strands are synthesized using the (−) strands as templates. At the latter step there is an amplification of (+) strands over (−) strand molecules. The (+) strand viral RNA molecule(s) are generally translated, at least in part, to yield virus-specific replicase. The (−) strands serve as the templates for subsequent synthesis of large numbers of (+) strands which may carry structural genes and which are destined to become encapsidated by coat protein. Structural proteins are translated from genomic RNA or from subgenomic RNA, depending on the virus. In the instance of the (+) strand viruses with multicomponent RNA genomes, the RNA molecules may be encapsidated in separate viral particles, in which case the host cell must be simultaneously infected with each component to yield a productive infection.

The plant (+) strand RNA viruses have been classified into two supergroups (R. Goldbach (1986) Ann. Rev. Phytopathol. 24:289). The picornavirus-like supergroup includes comoviruses, nepoviruses, and polyviruses, while the second supergroup includes those viruses which resemble the animal alphavirus Sindbis virus: the tobamoviruses, tobraviruses, bromoviruses, cucumoviruses, and alfalfa mosaic virus. Although the (+) strand RNA viruses of plants and animals are diverse with respect to host range, genome and particle structures, and exact mechanisms of viral replication, there are some amino acid and nucleic acid sequence homologies (reviewed in R. Goldbach (1987) Microbiol. Sci. 4:197). Amino acid sequence homologies have been described for poliovirus, foot-and-mouth disease and cowpea mosaic viruses (H. Franssen et al. (1984) EMBO J.3:855), and for nonstructural proteins encoded by brome mosaic virus, alfalfa mosaic virus, tobacco mosaic virus and Sindbis virus (J. Haseloff et al. (1984) Proc. Nat. Acad. Sci. USA 81:4358; P. Ahlquist et al. (1985) J. Virol. 53:536). The homologous regions within the nonstructural proteins are believed to reflect mechanistic similarities in the replication of viral nucleic acid and possibly evolutionary relationships.

The alphaviruses and the Sindbis-like plant viruses also share a common strategy for synthesis of coat protein (and in some cases for the synthesis of additional protein(s)). That strategy is the use of an internal promoter to direct the synthesis of ha (+) strand RNA molecule, called a subgenomic RNA, using the (−) strand as template. The subgenomic RNA comprises a subset of sequences found in the corresponding "genomic" (full-length) RNA, and may be encapsidated in viral particles. In the case of the brome mosaic virus (BMV), (+) strand RNA molecules outnumber the full-length (−) strand template about 100 to 1, and subgenomic and full-length genomic RNAs are made in approximately equimolar amounts (French and Ahlquist (1987) J. Virol. 61:1457). The subgenomic mRNA, which in BMV carries only the message for coat protein, is very effectively translated by the cellular protein synthetic machinery. For example, gram quantities of BMV-infected plant tissue synthesize milligram amounts of coat protein (L. Lane (1981) in *Handbook of Plant Virus Infections and Comparative Diagnosis,* E. Kurstak, Ed., Elsevier/North-Holland, Amsterdam, pp.333–376).

The bromoviruses are a group of (+) strand plant viruses with tripartite genomes. Included in this grouping are brome mosaic virus, cowpea chlorotic mosaic virus (CCMV), and broadbean mosaic virus (BBMV). CCMV and BBMV infect the dicots cowpeas and broadbeans respectively, and the host range of BMV is the grasses, including the cereals (L. C. Lane, (1981) in *The Handbook of Plant Virus Infections and Comparative Diagnosis,* Chapter 12, Elsevier, Amsterdam). Barley is a common experimental host for BMV, which has been well characterized.

BMV strain M1 (Madison 1) (P. Ahlquist et al. (1984) Proc. Nat. Acad. Sci. USA 81:7066) is the experimental system chosen to exemplify the present invention. The BMV genome is composed of three RNA molecules of unique, known sequence: RNA1 is 3234 bases in length, RNA2 is 2865 bases in length (P. Ahlquist et al. (1984) J. Mol. Biol. 172:369), and RNA3 is about 2114 bases in length (P. Ahlquist et al. (1981) J. Mol. Biol. 153:23). Complete cDNA clones have been produced (P. Ahlquist and M. Janda (1984) Mol. Cell. Biol. 4:2876). RNAs 1 and 2 are individually encapsidated; RNA3 is encapsidated together with RNA4, the 876 base subgenomic coat protein message which is presumed not to replicate in vivo (T. Lane (1974) Adv. Virus Res. 19:151). RNA molecules purified from virus particles and transcripts prepared from cloned viral cDNA sequences are infectious in the barley protoplast model system (P. Ahlquist et al. (1984) Proc. Nat. Acad. Sci. USA 81:7066). Therefore the full range of molecular biological techniques is available for the analysis of BMV nucleic acid functional sequences.

Experimental manipulations of the cloned BMV genome have begun to define regions of functional importance (P. Ahlquist and R. French (1988) in Domingo, Holland and Ahlquist (eds.) *RNA Genetics* Book 2: *RNA Variability*, chapter 3, CRC Press, Orlando, Fla.). Both RNAs 1 and 2 and their gene products are required for viral RNA synthesis; RNAs1 and 2 encode nonstructural proteins 1a and 2a respectively, and these proteins determine RNA-dependent RNA polymerase activity. RNA3 encodes nonstructural protein 3a and coat protein, but neither RNA3, protein 3a, nor coat protein is required for viral RNA replication (R. French and P. Ahlquist (1986) Science 231:1294). RNA3 can be modified by the insertion of a foreign gene in place of the coat protein gene, or by certain deletions, without the loss of replication ability (U.S. patent application Ser. No. 709,181, filed Mar. 7, 1985; R. French et al. (1986) Science 231:1294). RNA3 has been well studied because its gene products are not required for RNA replication (French et al. 1986). There are regions at the 5' and the 3' noncoding ends of the molecule which have homologs on RNAs 1 and 2, and it has been proposed that these sequences may function in viral RNA polymerase recognition, initiation of encapsidation, protection of the molecules from cellular nucleases, or a combination of these functions. Deletion studies using cloned cDNA and in vitro transcripts have shown that portions of the 5' and the 3' ends are required for genomic RNA replication, and that there is a graded effect of deletions in the intercistronic region of RNA3 as well (R. French and P. Ahlquist (1987) J. Virol. 61:1457). One feature of the intercistronic region is an oligo(A) tract, ranging from 16–22 nucleotides in length in natural virus populations (P. Ahlquist et al. (1981) J. Mol. Biol. 153:23). The subgenomic promoter of BMV is located in the intercistronic region as well. Neither the genomic nor the subgenomic promoters of the BMV are recognized by host RNA polymerases; only virally infected cells have RNA-dependent RNA polymerase activity capable of responding to these signals.

W. Miller et al., 1985, Nature 313:68, established that the production of RNA4, which serves as the message for coat protein, occurs by initiation of RNA synthesis within the RNA3 (–) strand molecule. (–) strand RNA3 templates ending at the BglII site about 21 bases upstream of the RNA4 initiation site were able to direct RNA4 production (Miller et al. (1985); L. Marsh et al. (1987) in *Positive Strand RNA Viruses*, New York, Alan R. Liss, Inc., pp.327–336. These studies and a study by R. French et al. (1986) Science 231:1294, show that deletions and insertions at or downstream of the SalI site, which is about 17 bases downstream of the start site, do not interfere with subgenomic mRNA production. French et al, 1986, demonstrated the expression of suitably inserted foreign genes by the subgenomic pathway. Thus, BMV subgenomic promoter activity was thought to be localized to a 37 base region which in the cDNA clone lies between the BglII and the SalI sites. Marsh et al. (1987) also presented evidence from in vitro experiments that the 5' boundary of the BMV subgenomic promoter activity was not further upstream than the BglII site about 21 bases upstream of the RNA4 start site. Marsh et al. (1987) also stated, without evidence, that the poly(A) tract somewhat further upstream of the RNA4 initiation site improved promoter activity. Both the studies by Miller et al. (1985) and those by Marsh et al. (1987) utilized in vitro expression experiments to examine the requirements of transcription; their results did not indicate that nucleotide sequence information as far upstream as –95 could contribute to the level of (+) strand mRNA synthesis. Neither Miller et al. (1985) nor Marsh et al. (1987) reported activity of subgenomic transcription, since in their constructs, sequences 5' to the putative promoter were missing. No published study has described the use of a subgenomic promoter-containing fragment of nucleic acid which could be transferred to a desired new location to generate a novel subgenomic mRNA.

SUMMARY OF THE INVENTION

The present invention teaches the use of the nucleotide sequences which function as a subgenomic promoter of a (+) strand RNA virus to direct the amplified expression of a structural gene in plant tissue, animal tissue or protist cells by RNA-dependent RNA polymerase. This is the first instance wherein the nucleotide sequences identifying the core region and an upstream activating domain of the subgenomic promoter of a (+) strand virus have been identified. This subgenomic promoter can be utilized in a modified virus, or in an appropriately engineered recombinant cDNA derivative which may be chromosomally integrated or maintained as an episome in transformed cells. The invention is exemplified by the subgenomic promoter of RNA3 of brome mosaic virus (BMV), but the teachings of the present invention allow a skilled artisan to select and use subgenomic promoter sequences from similar (+) strand RNA viruses for use in any desired cell type. The BMV subgenomic promoter is composed of two parts: the core promoter, identified by the nucleotide sequence from about –21 to about +16, as in FIG. 2, which is sufficient to direct subgenomic transcription, and an activating domain, identified by the nucleotide sequence from about –95 to about –22, as in FIG. 2. The activating domain best acts to increase the level of subgenomic transcription when said activating domain is located upstream of and in the proper orientation relative to said core promoter. Subgenomic transcription is dependent on RNA-dependent RNA polymerase activity and a (–) strand RNA molecule containing the subgenomic promoter and the structural gene; for example the BMV subgenomic promoter is recognized by RNA-dependent RNA polymerase activities encoded by RNA viruses including, but not limited to, brome mosaic virus and cowpea chlorotic mottle virus. Further improvements on the existing art are that upstream duplication of the activating domain of the subgenomic promoter can increase the level of subgenomic transcription over that directed by a single copy subgenomic promoter and that multiple copies of the subgenomic promoter can direct the synthesis of more than one subgenomic mRNA molecule from one (–) strand RNA template.

A principal object of the invention is to provide a recombinant DNA molecule containing a DNA copy of the subgenomic promoter of a (+) strand RNA virus and a structural gene, wherein the expression of said gene is a two step process: polII of a host cell transcribes a (–) strand RNA molecule carrying the functional sequence of the subgenomic promoter and the complementary sequence of said structural gene, wherein the synthesis of message-sense RNA is under the control of said subgenomic promoter. In one embodiment, the subgenomic promoter of RNA3 of brome mosaic virus directs the expression of a downstream structural gene. RNA polymerase II of the genetically modified plant tissue synthesizes an RNA molecule which is a (−) sense, functional copy of the subgenomic promoter and a (−) sense copy of the structural gene. An RNA-dependent RNA polymerase, which may be viral RNA replicase of BMV, recognizes the subgenomic promoter and synthesizes a (+) sense, or functional message-sense, RNA molecule which can then be translated into protein. The RNA-dependent RNA polymerase activity which responds to the BMV subgenomic promoter on the (−) strand RNA molecule may be from brome mosaic virus or cowpea chlorotic mottle virus genetic information, or from a recombinant DNA molecule encoding, for example, the 1a and 2a genes of BMV, wherein said genes may be translated into protein after transcription by RNA polymerase II of the host cell in response to either constitutive promoter or under the regulatory control of a plant regulatory element.

It is a further object of the invention to provide a method for the amplified gene expression in transformed cells composed of the steps of introducing into a desired host cell a recombinant DNA molecule containing a subgenomic promoter from a (+) strand RNA virus and a structural gene, wherein expression of the gene is under the regulatory control of the subgenomic promoter and wherein the expression of that gene depends on transcription by host cellular RNA polymerase II to yield a (−) strand RNA molecule carrying the active form of the subgenomic promoter and subsequent subgenomic transcription of the gene to yield active, (+) sense mRNA by RNA-dependent RNA polymerase activity, and then translation of the subgenomic transcript to produce the polypeptide encoded by the structural gene. The host polII transcription can be controlled by a constitutive, inducible or derepressible polII promoter.

In the figures, and throughout the application, the sequences which are the subgenomic promoter are presented as the (+) strand sequences, which will be understood to be the complement of the active subgenomic promoter sequences.

BRIEF DESCRIPTION OF THE FIGURES

FIG. 8 presents schematic representations of normal RNA virus replication an the two-stage expression system which utilizes the subgenomic promoter for amplified transcription.

DETAILED DESCRIPTION OF THE INVENTION

The following definitions are provided, in order to remove ambiguities to the intent of scope of their usage in the specification and claims.

An RNA virus, as used herein, means a virus whose genome is RNA in single-stranded form, the single strand being a (+), or messenger-sense strand. Replication of the viral (+) strand in a cell occurs by a process of direct RNA replication and is therefore distinguishable from the mechanism of retroviral replication which is characterized by an intermediate step of reverse transcription in the host cell.

Figure 1:
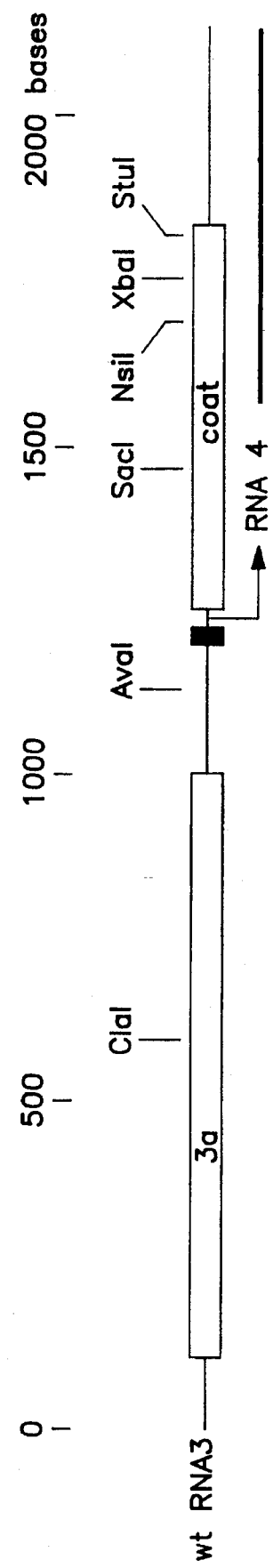
FIG. 1 presents a schematic map of BMV RNA3. Noncoding regions are shown as a single line, the 3a and coat genes as open boxes, the oligo(A) as a small filled box, and a bent arrow marks the position of the start of sequences encoding subgenomic RNA4. In keeping with common practice, the sequence of the packaged (+) strand is shown, but it should be noted that the complementary sequence serves as the template for subgenomic RNA synthesis. Numbering in this figure, and in FIGS. 3, 4, 5 and 6, subsequent figures, corresponds to that in the published sequence for RNA3 (P. Ahlquist et al. (1981) J. Mol. Biol. 153:23). Restriction endonuclease sites are recognized on the cDNA molecules carrying the RNA3 sequences.
Figure 2:
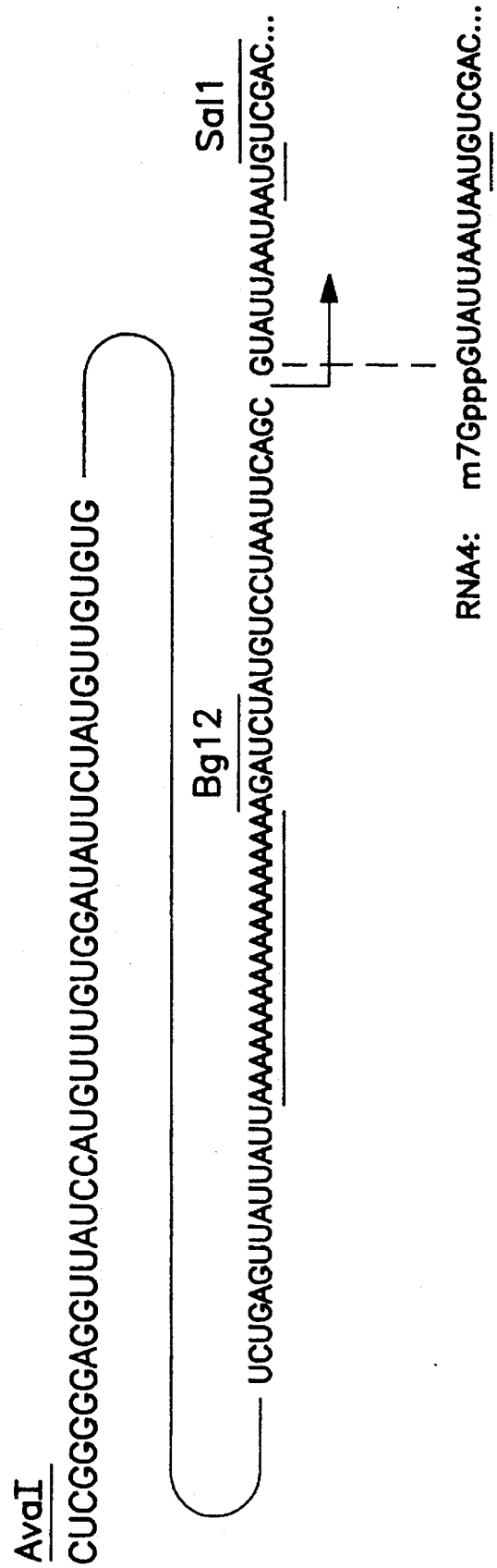
FIG. 2 displays the nucleotide sequence of the AvaI-SalI fragment of the RNA corresponding to the cDNA clone of brome mosaic virus RNA3, which fragment comprises the sequence of the BMV subgenomic promoter and the initiation site for subgenomic transcription in the (−) strand RNA molecule. The restriction sites shown are for the corresponding cDNA. Within the sequences shown the AvaI, BglII, and SalI sites bounding the core promoter are overlined and the coat protein initiation codon and the oligo(A) tract are underlined. A bent arrow marks the start of the subgenomic transcript (RNA4), and the sequence of the 5' end of the capped RNA4 molecule is given.

The term subgenomic promoter refers to those sequences within an RNA molecule and at the 5' end of a structural gene, which direct messenger RNA synthesis using said RNA molecule as the template. A subgenomic promoter is necessary to drive expression of genes using RNA as template; the subgenomic promoter is recognized by an RNA-dependent RNA polymerase, which may be a viral RNA replicase. The promoter itself may be a composite of segments derived from more than one source, naturally occurring or synthetic. It should be noted that a subgenomic promoter is located in relation to the particular gene whose transcription it initiates, and it is functionally recognized by an RNA-dependent RNA polymerase (or viral RNA replicase) when it is contained within an RNA molecule of the proper (−) polarity. The (−) sense RNA molecule containing the functional copy of the subgenomic promoter, which comprises the functional units of core promoter and activating domain, can be synthesized by RNA-dependent RNA polymerase using a (+) sense RNA molecule as template, or it may have been synthesized by (cellular) RNA polymerase II as a transcript initiated by a polII promoter. A specific embodiment of the present invention is the subgenomic promoter of RNA3 of brome mosaic virus (BMV). The identifying sequence of the subgenomic promoter of BMV is given in FIG. 2. For consistency herein, the position of the brome mosaic virus subgenomic promoter has been given relative to the start site of the subgenomic mRNA, which is designated +1. The BMV subgenomic promoter comprises the nucleotide sequence extending from about −95 to about +17, as in FIG. 2; the sequence comprised within the region from about −74 to about +16 also constitutes a functional subgenomic promoter.

The core promoter of a subgenomic promoter includes the minimum sequence required for function. In the case of BMV the core promoter comprises the nucleotide sequence from about −21 to about +17, as in FIG. 2. When correctly positioned as is understood in the art, the core promoter is sufficient to direct the initiation of message synthesis by an RNA-dependent RNA polymerase so that (+)strand RNA molecules are synthesized.

The activating domain of a subgenomic promoter includes sequences which increase the activity of the core promoter allowing for increased synthesis of subgenomic transcripts. In the case of BMV, the activating domain which can increase synthesis of mRNA directed by a subgenomic promoter, or a subgenomic core promoter, relative to the levels obtained when only the core promoter sequences are present, comprises the nucleotide sequence between about −95 and about −22, as in FIG. 2. Somewhat less activation is obtained with the sequence from about −74 to about −22.

RNA dependent RNA polymerase herein refers to an RNA synthetic enzyme which faithfully initiates (+) strand RNA synthesis in response to an RNA sequence which is a subgenomic promoter, and which is contained within a RNA molecule which is (−) sense relative to the coding region of the associated structural gene. For example, the 1a and 2a genes of BMV determine RNA-dependent RNA polymerase activity in cells within which those genes are expressed, and that RNA-dependent RNA polymerase activity recognizes subgenomic promoters including, but not limited to, those of brome mosaic virus and cowpea chlorotic mottle virus.

The term subgenomic transcription refers herein to the synthesis of RNA by an RNA-dependent RNA polymerase wherein said RNA-dependent RNA polymerase uses a (−) strand of RNA as template, and wherein said RNA-dependent RNA polymerase initiates the synthesis of mRNA in response to the nucleotide sequence information contained within the subgenomic promoter.

The term (+) strand RNA refers to RNA which is messenger-sense with respect to coding regions.

The term (−) sense RNA refers to sequences which are the complement of (+) sense molecules. For example, the (−) sense RNA molecule corresponding to a structural gene is complementary in sequence to the message, and the (−) sense RNA molecule cannot itself act as a message for the translation of the corresponding protein.

The term polII promoter herein refers to DNA sequences at the 5' end of genes which direct the initiation of transcription by the DNA-dependent enzyme RNA polymerase II of plant or animal cells. Promoter sequences are necessary, but not always sufficient, to drive the expression of downstream genes. The promoter itself may be a composite of segments derived from more than one source, naturally occurring or synthetic. Eukaryotic polII promoters are commonly identified by the presence of DNA sequences homologous to the canonical form 5'—TATAA—3' ("TATA" box) about 10–30 bp 5' to the location of the 5'-end of the mRNA (cap site, +1). About 30 bp 5' to the TATA box another promoter component sequence is often, but not always, found which is identified by the presence of DNA sequences homologous to the canonical form 5'-CCAAT–3'. For the purposes of the present description, a polII promoter is defined to include DNA sequence extending up to about 100 bp 5'(−100) to the cap site. Any additional sequences which may be located 5' to −100, and which may contain functionality including, but not limited to, that of transcription activating element or sequences exerting regulation in response to environmental stimuli, are considered promoter-associated elements, but for the purposes of this application, are considered part of the polII promoter, even though said sequences may be recognized by cellular proteins other than DNA-dependent RNA polymerase II. (A polymerase is said to "recognize" a particular DNA sequence if that sequence is necessary to or has regulatory effect on initiation of transcription by the polymerase.) It should be noted that a polII promoter is generally located 5' to the particular gene whose transcription it initiates. That transcript may be a (+) sense RNA molecule which can serve as a message or it may be a (−) strand RNA molecule which can serve as a template for subsequent RNA synthesis.

Expression refers to the transcription and translation of a structural gene so that a protein is made. Gene expression can be assessed by direct detection of the protein product, by protein gel electrophoresis or immunological methods, for example. Oftentimes, expression is assessed by detection of the mRNA products of transcription. This method is particularly appropriate for the assessment of transcriptional control factors, such as promoter elements, since the effects of nontranscriptional processes, such as protein degradation, are excluded.

A structural gene refers to the combination of nucleotide sequences encoding a protein and (some of) the regulatory sequences which allow expression of that structural gene in a plant cell or tissue. The term structural gene refers to that portion of a gene composed of a DNA segment coding for a protein, polypeptide or portion thereof, possibly including a ribosome binding site and/or translational start codon. The term can also refer to copies of a structural gene naturally found within the cell, but artificially introduced. In this case a structural gene naturally found in a cell may be reintroduced into a cell as part of a chimeric gene having non-natural regulatory control sequences, for example under the control of the BMV subgenomic promoter. The structural gene may encode a protein not normally found in the plant cell in which the gene is introduced, in which case it is termed a foreign structural gene. A foreign structural gene may be derived in whole or part from a bacterial genome or episome, eukaryotic nuclear or plastid DNA, cDNA, viral DNA, or chemically synthesized DNA. It is further contemplated that a structural gene may contain one or more modifications in either the coding segments or in the untranslated regions which could affect the biological activity or the chemical structure of the expression product, the rate of expression, or the manner of expression control. Such modifications include, but are not limited to, insertions, deletions and substitutions of one or more nucleotides. The structural gene may constitute an uninterrupted coding sequence or it may include one or more introns, bounded by host cell-functional splice junctions. The structural gene may be a composite of segments derived from a plurality of sources, naturally occurring or synthetic. That structural gene may also produce a fusion protein. It is contemplated that the introduction into host cells of recombinant DNA containing the structural gene in combination with a subgenomic promoter or with a polII promoter will include constructions in which the structural gene is not derived from the same kind of cell as the host, and constructions wherein additional copies of naturally occurring genes are expressed under BMV subgenomic promoter control.

Figure 3:
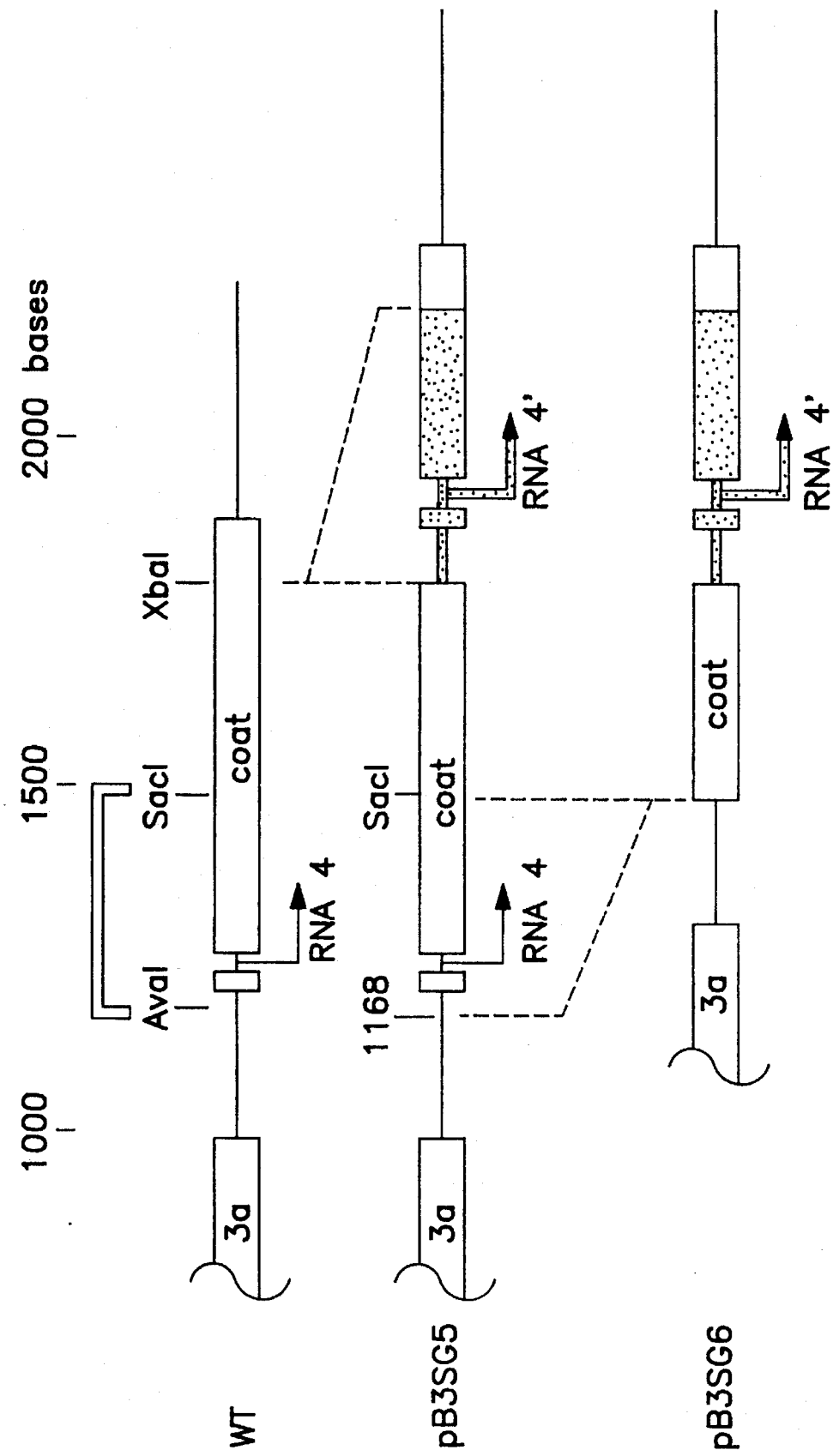
FIG. 3. Schematic diagram of the regions surrounding the coat gene cDNA in plasmids pB3TP8 (wild-type), pB3SG5, and pB3SG6. The AvaI-SacI fragment duplicated in pB3SG5 is bracketed over the wild-type sequence and shaded in its new locations in pB3SG5 and pB3SG6. Initiation sites for subgenomic RNAs 4 and 4' are shown by bent arrows. For pB3SG5 and pB3SG6, the RNA4':RNA3 ratios were 2.4 and 3.3 respectively. For the wild-type plasmid and pB3SG5 the RNA4 :RNA3 ratios were 1.2 and 0.4, respectively.

A recombinant DNA molecule is one which has been either naturally or artificially produced from parts derived from heterologous sources, which parts may be naturally occurring or chemically synthesized molecules, and wherein those parts have been joined by ligation or other means known to the art.

Plant tissue includes differentiated and undifferentiated tissues of plants including, but not limited to, roots, shoots, leaves, pollen, seeds, tumor tissue such as crown galls, and various forms of aggregations of plant cells in culture such as embryos and calli. The plant tissue may be in planta, or in organ, tissue, or cell culture.

The term chemically synthesized, as related to a sequence of DNA, means that the component nucleotides were assembled in vitro using nonenzymatic means. Manual synthesis of DNA may be accomplished using well established procedures (i.e. M. Caruthers (1983) in *Methodology of DNA and RNA Sequencing,* Weissman (ed.), Praeger Publishers (New York) Chapter 1) or automated synthesis can be performed using one of a number of commercially available machines.

Homology as used herein, refers to identity of nucleotide sequences. The extent of homology between DNA sequences can be empirically determined in DNA hybridization experiments, such as those described in B. Hames and S. Higgins (1985) *Nucleic Acid Hybridisation,* IRL Press, Oxford, UK.

Because there is some flexibility with respect to the sequences carried on BMV RNA3, it was possible to examine how certain RNA sequences in the intercistronic region contributed to subgenomic promoter activity. It was known that initiation of subgenomic RNA synthesis does not require more than 16 bases downstream of the start site (i.e. 3' to the start of RNA4 sequences in the virion-sense RNA) (W. Miller et al. (1985) Nature 313:68; R. French et al. (1986) Science 231:1294; L. Marsh et al. (1987) in *Positive Strand RNA Viruses,* Alan R. Liss, Inc., New York, pp.327–336). Infectious in vitro transcripts synthesized from engineered RNA3 cDNA clones were used to determine the effects of alterations in the primary structure of RNA3. A restriction map of the cDNA clone of BMV RNA3 and the nucleotide sequence of the AvaI-SalI region surrounding the subgenomic transcript start sites are given in FIGS. 1 and 2. A notable feature of the sequence upstream from the subgenomic message start site is an oligo(A) tract which is conserved at equivalent genomic positions in other members of the bromovirus group (P. Ahlquist et al. (1981) Cell 23:183; unpublished observations). To determine whether the oligo(A) tract affects subgenomic promoter activity, mutant plasmid pB3IC4, which lacks all but one A residue, was constructed. That in vitro RNA3 transcript possessed less than 10% of the parental subgenomic promoter activity in vivo. The length of the oligo(A) tract ranges in length from 16–22 in natural RNA3 populations (P. Ahlquist et al. (1981) J. Mol. Biol. 153:23). In pB3TP8 there are 18 A residues (M. Janda et al. (1987) Virology 158:259). Subgenomic promoters containing oligo(A) tracts differing in length from the 18 as in FIG. 2, will be considered functionally equivalent to the BMV subgenomic promoter of FIG. 2, provided that similar amounts of sequence information flanking the oligo(A) are maintained.

In the test system, parental RNA3 transcripts produced progeny (+) strand RNAs at a ratio of RNA4:RNA3 of 1.2. To separate the effects of sequence changes in the intercistronic region on subgenomic message production from effects on genomic RNA3 amplification, a second subgenomic initiation site was established by inserting the AvaI-SacI fragment of cDNA spanning the start site at the XbaI site of the RNA3 cDNA to create pB3SG5 (FIG. 3). pB3SG5 transcripts were replicated, and directed the synthesis of two subgenomic RNAs as intended. The subgenomic mRNA produced from the engineered copy of the subgenomic promoter (RNA4') was more abundant than both the genomic RNA3 and the subgenomic mRNA originating from the wild-type subgenomic promoter. A ratio of RNA4':RNA3 of 2.4:1 was obtained from pB3SG5. pB3SG6, which contained only one copy of the subgenomic promoter at the same distal location as that of pB3SG5, produced subgenomic and genomic RNAs at a ratio of 2.5:1.

The sizes of subgenomic RNA species obtained with pB3SG5 and pB3SG6 were consistent with initiation from the expected sites in the duplicated promoter sequences. Primer extension experiments confirmed that the initiation site for subgenomic RNA synthesis was unchanged even when the subgenomic promoter was moved to a new location or was duplicated within the RNA3 cDNA clone. Like wild-type RNA4 (R. Dasgupta et al. (1976) J. Virol. 18:260), the subgenomic RNA produced from the novel subgenomic RNA initiation site was capped.

Figure 4:
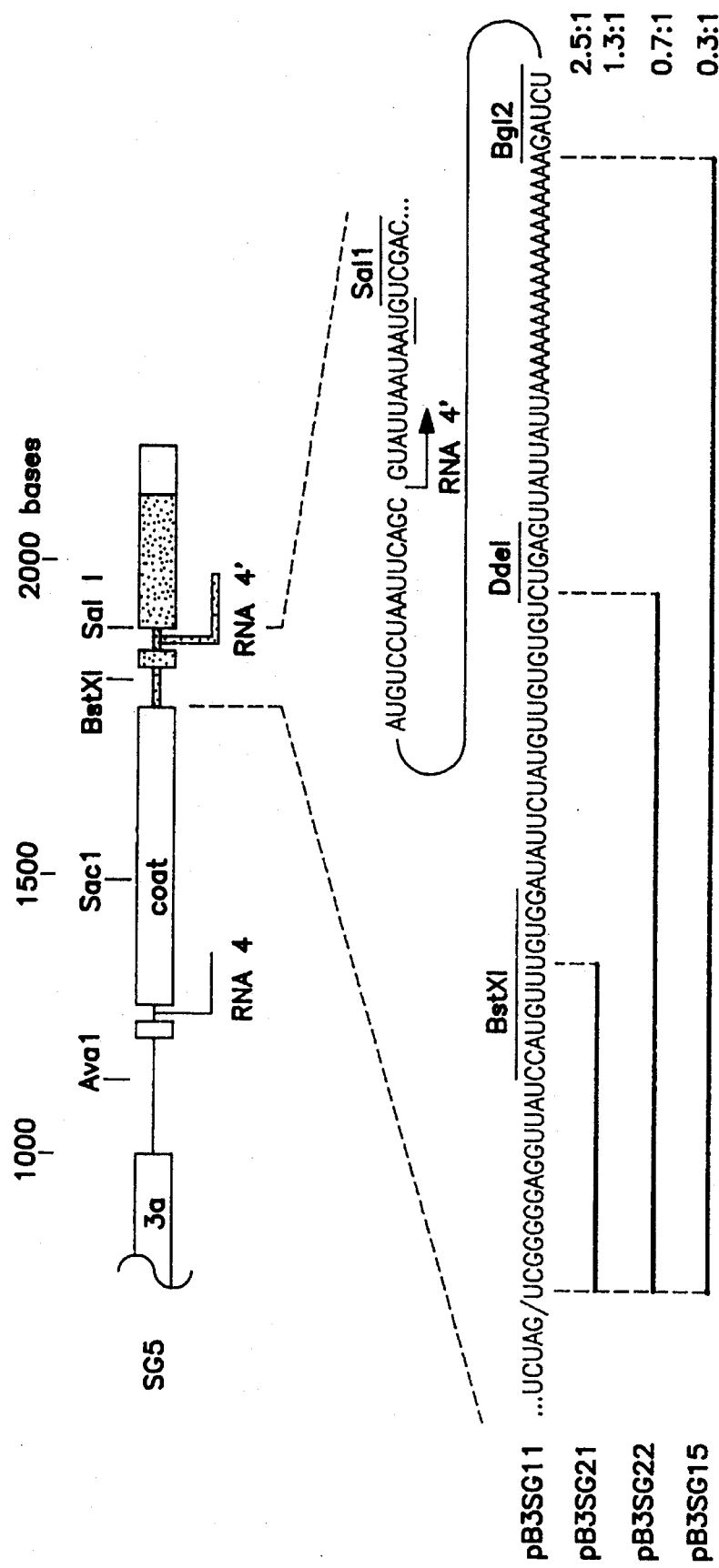
FIG. 4. Effects of 5' deletions on subgenomic promoter activity. The sequence surrounding the 3' proximal RNA initiation site in derivative pB3SG5, and map of deletions in derivatives pB3SG21, 22, and 15. pB3SG11 is the plasmid which represents the undeleted sequences. Values given for the molar ratios of RNA4':RNA3 are the averages of two or more independent experiments.

Further functionality of RNA sequences in the region upstream of the subgenomic RNA start site was examined by determining the effects of a series of internal insertion and deletion mutations on subgenomic mRNA synthesis in plant tissue. A second functional subgenomic promoter was established distal to the intercistronic region; therefore, it was possible to use deletion analysis to investigate the 5' limits of sequences contributing to subgenomic RNA synthesis without significant affects on full-length RNA3 accumulation. In protoplast infections these deletions induced an obvious progressive decline in subgenomic RNA production as the deletions extended further 5'. The decreased accumulation must reflect reduced synthesis because the sequence of the subgenomic RNA, and therefore its stability, was unchanged in the various constructions. The results are summarized in FIG. 4. pB3SG11 carried the AvaI-SalI fragment containing about 95 bases upstream of through about 16 bases downstream of the start of subgenomic transcription. The RNA4':RNA3 ratio of 2.5 was similar to that of pB3SG5, which carried the sequence information through the SacI site well into the coat protein gene. pB3SG21, containing subgenomic promoter sequences from the BstXI site about −74 through the SalI site downstream of the start site, produced an RNA4':RNA3 ratio similar to the RNA4:RNA3 ratio of the wild-type plasmid, but lower than that of pB3SG11. Further deletions of the upstream region gave further decreases in the RNA4':RNA3 ratios. pB3SG15 was the plasmid with the shortest subgenomic promoter fragment (BglII-SalI); the RNA4':RNA3 ratio was 0.3:1, showing that the efficiency of the truncated subgenomic promoter was limited. Thus, the 5' end of the core promoter is no further 5' than −21, and all information necessary for efficient initiation is 3' to about −95, with results similar to that of the wild-type plasmid ratio when only about 74 bases of upstream information are present. Therefore, the BglII-SalI fragment, from about −21 to about +16 as in FIG. 2, comprises the BMV subgenomic core promoter. The AvaI-SalI fragment, from about −95 to about +16, as in FIG. 2, and the BstXI-SalI fragment, from about −74 to about +16, as in FIG. 2, both contain activating domain and core promoter activities of the subgenomic promoter.

Figure 5:
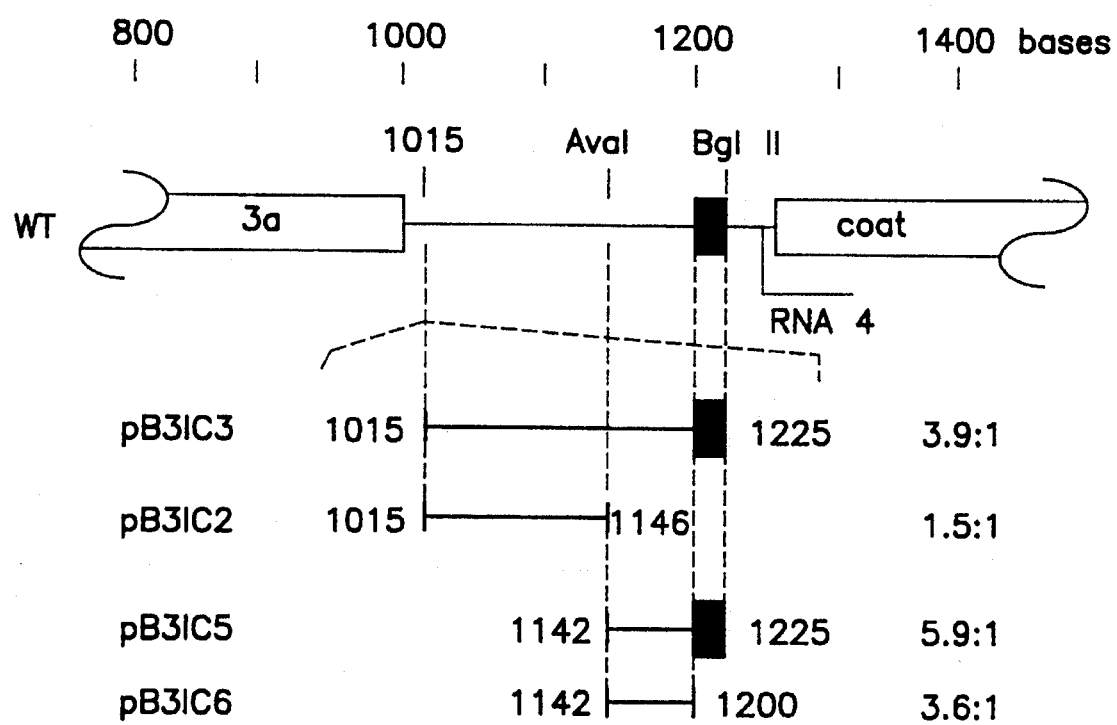
FIG. 5. Effects of upstream duplications on subgenomic promoter activity. Map of the intercistronic region of wild-type RNA3 (wt) and sequences duplicated in RNA3 derivatives pB3IC2, 5, and 6. In each of these derivatives the indicated segment of intercistronic sequence is inserted as a duplication immediately 5' to position 1015 in the RNA3 sequence. Values given for the molar ratios of RNA4':RNA3 are the averages of three independent experiments. For comparison, RNA4':RNA3 ratios obtained with no duplications of upstream information are generally about 2.4 for similar constructions.

Duplication of subgenomic promoter activating domain sequences from the RNA3 intercistronic region at a site some 220 bases upstream of the start site for subgenomic transcription led to a stimulation in subgenomic RNA synthesis. The structures and the RNA4:RNA3 ratios for wild-type and the mutant plasmids is given in FIG. 5. Significant stimulation of subgenomic RNA synthesis was achieved by duplicating the sequence contained within the activating domain, an AvaI-BglII fragment from about −95 to about −21 of the cDNA of RNA3 upstream of RNA start site. While the oligo(A) tract contributed to that stimulation, it was not required for stimulation to occur.

Figure 6:
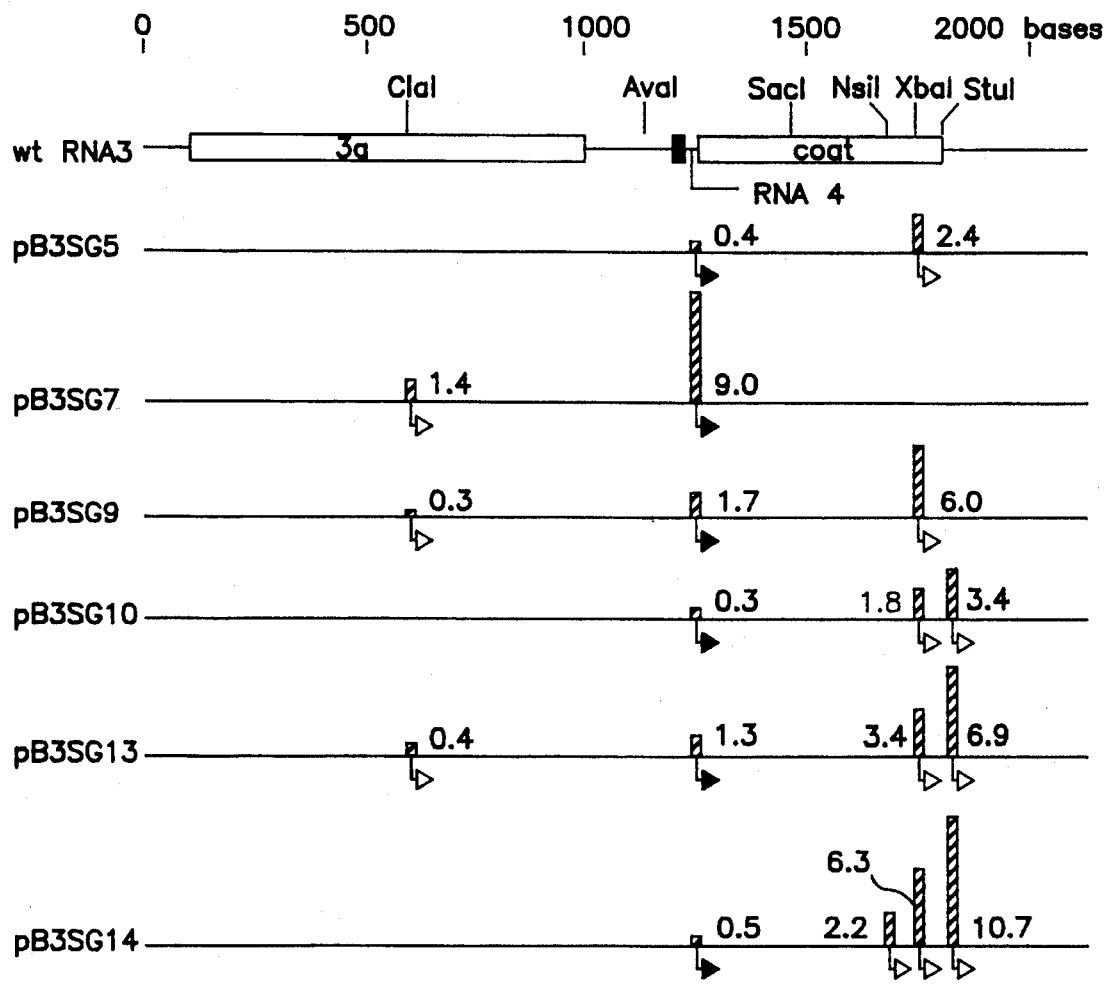
FIG. 6. Production of multiple subgenomic transcripts from individual RNA3 derivatives. Schematic maps of RNA3 derivatives pB3SG5, 7, 9, 10, 13, and 14. On each line open- headed arrows indicate the sites of insertion of additional copies of the AvaI-SacI fragment spanning the RNA4 initiation site. Above each arrow is given the molar ratio of that subgenomic RNA to the genomic RNA3 derivative, averaged from two or more independent experiments. Each value is also represented as a histogram bar for visual comparison. Arrows with filled heads represent the unaltered RNA4 promoter in its wild-type context. The average ratio of subgenomic RNA4 to genomic RNA3 production in wild-type infection under these conditions is 1.2.

To determine whether sites other than the XbaI site could support subgenomic RNA synthesis when the AvaI-SacI fragment was present, the AvaI-SacI fragment of RNA3 was duplicated at a ClaI site 5' to the normal RNA4 start site in pB3SG7. Both subgenomic promoters were functional, and as in other cases where there were two copies of the subgenomic promoter, the smaller of the subgenomic RNAs was more abundant. Mutant RNA3 cDNA clones were also constructed to test whether more than two subgenomic promoters were functional in a single RNA3 derivative. pB3SG9 and pB3SG10 each contained two AvaI-SacI subgenomic promoter fragments while pB3SG13 and pB3SG14 each contained three. It was found that the subgenomic promoter was active at each location tested, and a distinct gradient favoring greater accumulation of subgenomic RNAs from 3' proximal sites was observed in these experiments (FIG. 6). The observed activation of subgenomic transcription is a consequence of upstream duplications of subgenomic promoter components.

The ability of the subgenomic promoter fragment to function in the reverse orientation relative to the surrounding cDNA was tested in pB3SG5R and pB3SG6R. No putative subgenomic RNA species were observed. In both cases the inversion caused severe inhibition of RNA3 accumulation. For SG6R, with its 26 b inverted repeat, only a small amount of RNA3 could be detected on overexposures of the autoradiographs, but SG5R with its 330 bp inverted repeat never gave detectable RNA3 production. No internally initiated "pseudo-subgenomic" RNA species of negative polarity were detected from either construction.

Figure 7A:
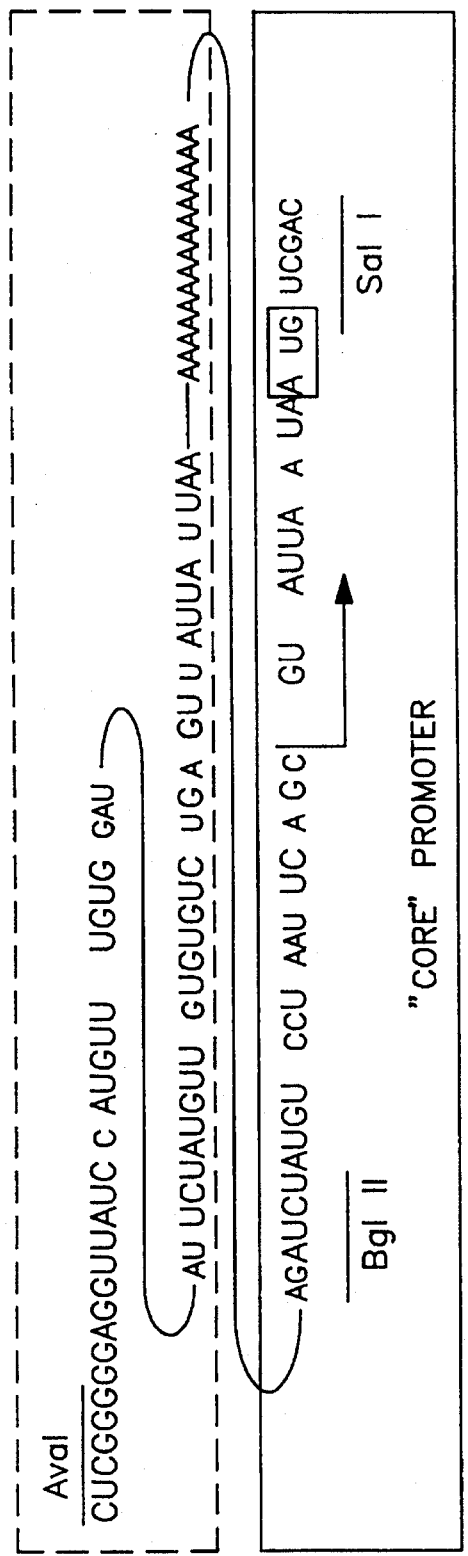
FIG. 7(A). Alignment of the AvaI-SalI sequence of BMV RNA3 to emphasize the presence of imperfect direct repeats. This analysis was computer-assisted. The BglII-SalI core promoter sequence is shown within the indicated solid box. The coat initiation codon, overlapping the SalI site, is also marked.
Figure 7B:
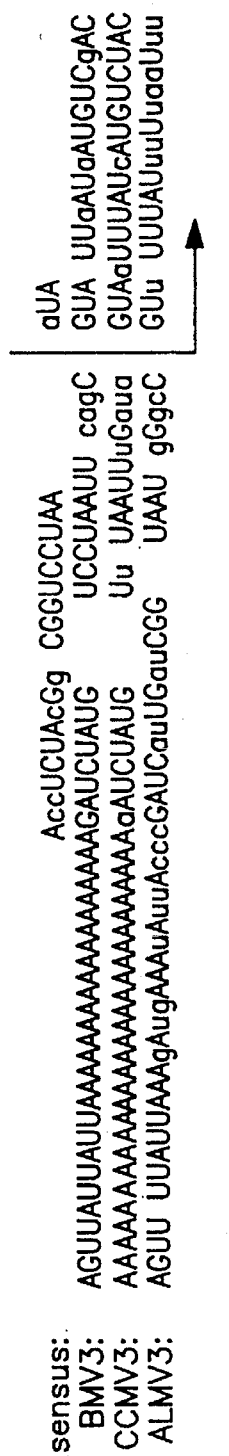
FIG. 7(B). Sequence alignment showing the similarity among BMV, the animal alphaviruses, cowpea chlorotic mottle virus (CCMV), and alfalfa mosaic virus (ALMV) genomic RNAs near the start of sequences encoding subgenomic mRNAs for capsid proteins. There is a large gap in each plant virus sequence introduced solely to achieve alignment with the alphavirus consensus sequence. The bent arrow shows the start of subgenomic RNA sequences and the initiation codons of the BMV and CCMV coat protein genes are underlined. These alignments were generated by computer using published sequences; in no virus other than BMV has the actual subgenomic promoter been empirically determined. The alphavirus consensus was derived from the sequences of Sindbis, Middelburg, Semliki Forest, and Ross River viruses (J.-H. Ou et al. (1982) Proc. Natl. Acad. Sci. USA 79:5235). The ALMV RNA3 sequence is from R. Barker et al. (1983) Nucleic Acids Res. 11:2881, and the CCMV RNA3 sequence was determined by P. Ahlquist et al. (1981) Cell 23:183.
Figure 8A:
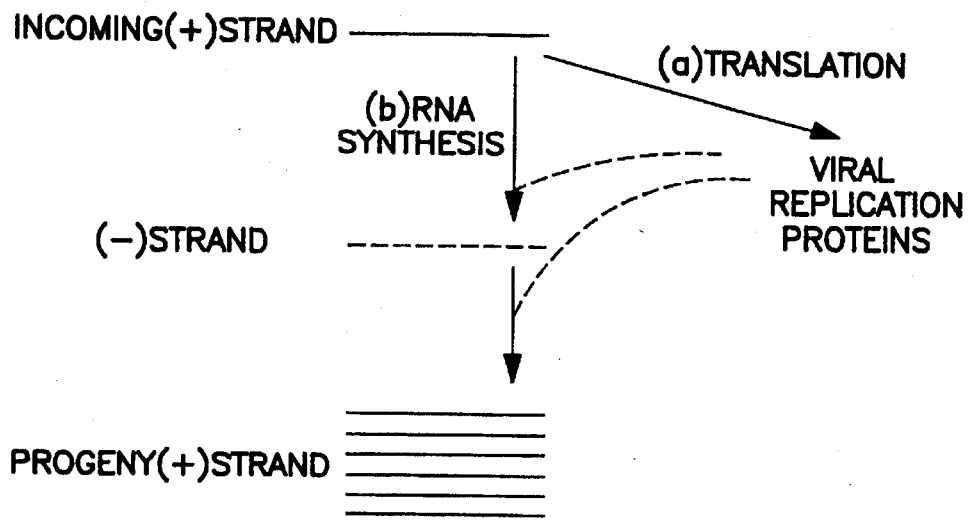
FIG. 8A gives the schematic of successive (−) and (+) strand synthesis amplifying viral RNA in normal infection of host cells.
Figure 8B:
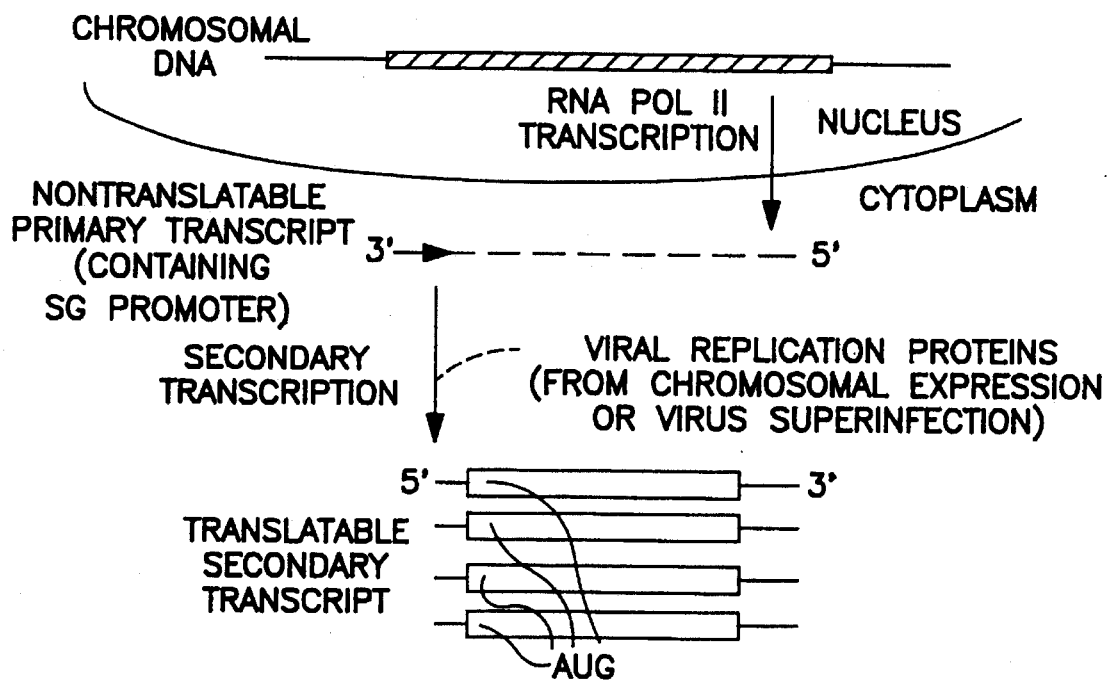
FIG. 8B gives the schematic for the similar amplification of a chromosomal transcript by cytoplasmic synthesis of multiple complementary copies from a viral subgenomic promoter. The nontranslatable primary transcript, which itself is a (−) strand with respect to the coding sequence of the plant-expressible gene, is synthesized by cellular RNA polymerase II in response to a polII promoter. RNA-dependent RNA polymerase activity, such as that induced by the 1a and 2a genes of BMV, is necessary to achieve subgenomic transcription of a (+) sense mRNA directed by the subgenomic promoter sequences present in active form on the (−) strand primary transcript RNA molecule. The plant tissue can be genetically modified to contain the gene(s) encoding RNA-dependent RNA polymerase activity under the regulatory control of RNA polymerase II, or that activity can be expressed during viral infection. Because the polarity of the primary transcript is opposite to its product subgenomic RNA, translation of appropriately oriented genes only occurs from the secondary subgenomic transcript. Thus, this scheme provides control of induction as well as amplifying expression.

Computer-assisted sequence inspection revealed that the 120 base AvaI-SalI region of the RNA3 cDNA, which contains the core promoter and the activating domain of the subgenomic promoter, includes several imperfect direct repeats (FIG. 7). The 30 bases overlapping and immediately 5' to the oligo(A) tract have 67% identity with the BglII-SalI core promoter region, with the 3' boundary of this duplication corresponding precisely to the start of the coat protein coding region. Immediately 5' to this duplication is a clearly related segment which also includes a single-mismatch repeat of the consensus element 5'—AUCUAUGUU—3'. Thus, nearly all of the AvaI-SalI promoter region consists of repeats or partial repeats of sequences related to the core promoter, punctuated in one area by the oligo(A). Although similar in sequence, the two copies of the core promoter motif flanking the oligo(A) were clearly not equivalent. While the 3' copy contains a weak but functional promoter, no subgenomic RNA initiation was detected at the corresponding site in the 5' copy of this motif.

As shown in FIG. 7, the oligo(A)/core promoter region of BMV RNA3 contains similarities to the analogous regions near the subgenomic mRNA start sites in some other plant RNA viruses, including cowpea chlorotic mottle virus (CCMV) and alfalfa mosaic virus (AMV). BMV is the only (+) strand RNA virus for which the subgenomic promoter sequences have been determined experimentally. FIG. 7 also displays the significant homology of the sequence from the BMV subgenomic promoter region to the consensus sequence from just upstream of the start of alphavirus subgenomic RNA (taken from J.-H. Ou et al. (1982) Proc. Natl. Acad. Sci. USA 79:5235–5239); the functionality of the alphavirus consensus sequence in directing subgenomic RNA synthesis has not been tested. The sequence similarities shown in FIG. 7 overlap the BMV consensus element AUCUAUGUU which, with single mismatches, is repeated three times in the BMV AvaI-SalI fragment (FIG. 7A). Deletions of the upstream repeated sequences (FIG. 4) resulted in decreased subgenomic promoter activity. Furthermore, RNA4 synthesis was shown to proceed correctly from a CCMV RNA3 when BMV RNAs1 and 2 were provided in a co-infection and similarly, co-infections of BMV RNA3 with CCMV RNAs 1 and 2 yield accurately synthesized RNA4. Previously published studies of BMV subgenomic transcription were based on in vitro experiments carried out using extracts made from BMV-infected barley cells (L. Marsh et al. (1987) in *Positive Strand RNA Viruses,* Alan R. Liss, Inc., New York; W. Miller et al. (1985) Nature 313:68). The work of the present invention was performed using in vivo experiments to study subgenomic RNA synthesis. The current results demonstrate that the BglII-SalI region of cDNA for BMV RNA3 has some subgenomic promoter activity in vivo, however, sequence information upstream of the BglII site (the AvaI-BglII region from about −95 to about −21 relative to the start site) constitutes an activating domain which is required for efficient synthesis of subgenomic RNA by RNA-dependent RNA polymerase. In addition, the work of the present invention demonstrated that a fragment of DNA (e.g., the AvaI-SalI fragment) containing the subgenomic promoter could be moved to a novel location within an RNA sequence with subgenomic promoter activity retained. Furthermore, several subgenomic promoters have now been shown to be functional within a single RNA3 derivative even if located at separate sites leading to a plurality of subgenomic RNA transcripts. Still further, it was determined that a fragment carrying the activating domain of a subgenomic promoter could be duplicated upstream of the subgenomic promoter with the unexpected result that subgenomic transcription was enhanced.

A principal feature of the present invention is the brome mosaic virus subgenomic promoter, which is identified by the nucleotide sequence as in FIG. 2, nucleotides −95 to +16 relative to the start site for subgenomic transcription. This nucleotide sequence was sufficient to direct subgenomic RNA synthesis from a novel site on the viral genome at wild-type or greater levels. Sequences no more than about 20 bases upstream of the start site sufficed to direct specific initiation at a low level; therefore the region between −21 and +16 is termed the subgenomic core promoter. Sequences at least as far as 74, but no more than 95 bases upstream are required for full promoter activity. The oligo(A) tract within the region between −21 and −74 is an important functional element in full subgenomic promoter activity, and may function as a recognition sequence element or may provide spacing or flexibility between other elements of the promoter. The function of the sequence elements with homology to the consensus element AUCUAUGUU is not known, but analogy to DNA-dependent transcription suggests that these sequences might be recognized by trans-acting factor(s) to increase the level of subgenomic transcription. Further increases in the level of subgenomic transcription were obtained by duplicating the sequence information of the AvaI-BglII fragment upstream from the start site, as in FIGS. 2 and 5. The subgenomic promoter can be used to direct the expression of a structural gene when the subgenomic promoter is in a site other than its normal site within the RNA3 derivative, and enhancement of subgenomic transcription may be achieved by duplication of the activating domain portion of the subgenomic promoter.

From the data presented herein, location, isolation and use of subgenomic promoters from other sources can be readily carried out by those of ordinary skill in the art without undue experimentation. The comparative sequence data of FIG. 7 show remarkable homology over a wide range of RNA sources known to possess subgenomic promoters. From such data, together with known or readily obtainable data on subgenomic transcription start sites, subgenomic promoters equivalent to that of BMV RNA3 can be isolated and used as described and exemplified herein. The recognized homology and mode of action of RNA-dependent RNA polymerases allows for the mixed combination of subgenomic promoter and RNA-dependent RNA polymerase from heterologous sources, or demonstrated herein for BMV and CCMV. However, it will be understood that differences in rate of transcription and promoter specificity can lead to quantitative differences in expression, depending on the particular combination of promoter and polymerase employed.

It is an object of this invention to provide a method for the amplified expression in plant tissue of a structural gene under the regulatory control of an RNA virus subgenomic promoter, which in one embodiment can be the subgenomic promoter of brome mosaic virus. The method is composed of the following steps: introducing into plant tissue a recombinant DNA molecule containing the subgenomic promoter and a structural gene such that the expression of said gene is under the regulatory control of the subgenomic promoter and the entire combination is of a conventional polII promoter, either constitutive, inducible or derepressible, synthesis by cellular RNA polymerase II of a primary, (−) strand transcript containing the subgenomic promoter in its active form and the complement of the coding sequence of the structural gene, and expression of RNA-dependent RNA polymerase activity (for example, by the infection of the modified plant tissue with brome mosaic virus, or by inducing chromosomally integrated copies of the BMV 1*a* and 2*a* genes under the control of polII promoters), followed by subgenomic transcription to yield a secondary, (+) sense mRNA encoding the structural gene which is then translated to yield its protein product. This scheme has the advantage that in the absence of RNA-dependent RNA polymerase activity the structural gene is completely silent because there is no (+) sense RNA synthesized, and therefore, there can be no translation to yield the protein product of that gene. Generally genes under the regulatory control of regulated polII promoters and associated sequence elements exhibit some degree of expression even in the absence of inducing conditions. Use of a subgenomic promoter is therefore useful to prevent expression of a gene which would be lethal for the cell which expresses it. When such a gene is tightly controlled so that it is only expressed after infection with virus, its expression kills the infected cell before virus replication and dissemination occur. This process constitutes an effective means for controlling virus infection in plant tissue, and therefore a way to prevent crop damage and economic loss. The advantages of this scheme would be lost if the control of lethal gene expression were not virtually absolute, and are therefore not feasible with prior art polII promoters.

Another consequence of the use of a subgenomic promoter is the rapid amplification of expression once an active RNA-dependent RNA polymerase is present. The promoter is therefore useful to express any gene when a sudden burst of expression is desired. For example, rapid but transitory expression of high-level herbicide resistance can be obtained by providing a herbicide-resistance gene under subgenomic promoter control and an RNA-dependent RNA polymerase under control of an inducible or derepressible polII promoter. The latter can be chosen to turn on polymerase expression in response to a component in the herbicide formulation. Other specific resistances can be regulated in a similar manner and will be especially useful where the resistance is the result of expressing a gene that leads to production of a toxic distasteful or otherwise undesirable substance. High level, transitory expression of such a gene can be achieved using an innocuous inducing agent, so as to produce the desired resistance at precisely the desired stage in the host organism's life cycle. Later, for example at harvest, when the gene is not expressed, the undesirable substance is absent from plant tissue intended for consumption.

It will be understood by those of ordinary skill in the art that the use of subgenomic promoter-structural gene combinations is not confined to plants. Positive strand RNA viruses exist for bacteria and animal cells as well as plants, and subgenomic promoter homology is seen for both plant and animal viruses. Therefore, expression of a structural gene under subgenomic promoter control can be accomplished in any transformable cell including, without limitation, plant cells, animal cells and bacterial cells.

The production of genetically modified plant tissue containing and expressing a structural gene under the transcriptional control of the BMV subgenomic promoter combines the specific teachings of the present disclosure with a variety of techniques and expedients known in the art. In most instances, alternative expedients exist for each stage of the process. The choice of expedients depends on variables such as the choice of vector system for the introduction and stable maintenance of the expression complex, the cell type, whether plant, animal or protist, to be modified and, in the case of plants, the desired regeneration strategy, and the particular structural gene to be used, all of which present alternative process steps which those of ordinary skill in the art are able to select and use to achieve a desired result.

Homologs of structural genes or of other sequences may be identified by the ability of their nucleic acids to cross-hybridize under conditions of appropriate stringency as is well understood in the art. It will be understood that there may be minor sequence variations within sequences utilized or disclosed in the present application. It is well known in the art that some DNA sequences within a larger stretch of sequence are more important than others in determining functionality. A skilled artisan can test allowable variations in sequence, without undue experimentation, by well known mutagenic techniques which include, but are not limited to, those discussed by D. Shortle et al. (1981) Ann. Rev. Genet. 15:265; M. Smith (1985) ibid. 19:423; D. Botstein and D. Shortle (1985) Science 229:1193; by linker scanning mutagenesis (S. McKnight and R. Kingsbury (1982) Science 217:316) or by saturation mutagenesis (R. Myers et al. (1986) Science 232:613). These variations may be determined by standard techniques in combination with assay methods described herein to enable those skilled in the art to manipulate and bring into utility the functional units of polII promoters, structural genes, and subgenomic promoters. Using the methods described herein the skilled artisan can, without undue experimentation, test altered sequences within a subgenomic promoter for retention of function. The final steps of the preferred embodiment for obtaining genetically modified plant tissue include inserting the expression complex into a T-DNA-containing vector, and transferring the recombinant DNA to plant tissue wherein the modified T-DNA becomes stably integrated as a part of the genome. Other techniques for transforming plant cells, including protoplast transformation, electroporation, micro-injection and agroinfection can be employed.

The following examples are provided for illustrative purposes only and are not intended to limit the scope of the invention. The examples utilize many techniques well known and accessible to those skilled in the arts of molecular biology, in the manipulation of recombinant DNA in plant tissue, and in the culture and regeneration of transformed plants. Techniques for similar manipulations of recombinant DNA in animal and bacterial cells are well known. Enzymes are obtained from commercial sources and are used according to the vendors' recommendations or other variations known in the art. Reagents, buffers, and cultural conditions are also known to the art. References containing standard molecular biological procedures include T. Maniatis et al. (1982) *Molecular Cloning,* Cold Spring Harbor Laboratory, Cold Spring Harbor, N.Y.; R. Wu (ed.) (1979) Meth. Enzymol. 68; R. Wu et al. (eds.) (1983) Methods Enzymol. 100 and 101; L. Grossman and K. Moldave (eds.) Methods Enzymol. (1980) 65; J. Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley, Calif.; R. Schlief and P. Wensink (1982) *Practical Methods in Molecular Biology,* Springer-Verlaz Berlin Glover (ed.) (1985) *DNA Cloning,* Vols. I and II, IRL Press, Oxford, UK; B. Hames and S. Higgins (eds.) (1985) *Nucleic Acid Hybridization,* IRL Press, Oxford, UK; P. Setlow and A. Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

EXAMPLE 1

This example describes the recombinant DNA molecules and the cloning strategies used to characterize the BMV subgenomic promoter sequences.

1.1 Wild-Type cDNA Clones of Brome Mosaic Virus in Transcription Vector Plasmids Plasmids pB1TP3, pB2TP5, and pB3TP8 contain cDNA copies of BMV RNAs 1, 2, and 3, respectively, from which properly initiated, capped and infectious transcripts of the complete BMV genome can be produced with T7 RNA polymerase (M. Janda et al. (1987) Virol. 158:259). Other plasmids used in the construction of RNA3 derivatives were pB3TP7 (M. Janda et al. (1987) and pB3PM1 (P. Ahlquist and M. Janda (1984) Mol. Cell. Biol. 4:2876–2882). Those plasmids contain the same BMV cDNA region as pB3TP8, but are linked to a T7 promoter with a single intervening G residue, and linked directly to an E. coli promoter, respectively. All the above plasmids except pB3M1 are pUC119 derivatives, and so contain the ssDNA replication origin of bacteriophage M13, allowing recovery of ssDNA forms after superinfection with suitable helper phage, such as M13K07 (provided by J. Vieira).

1.2 Plasmid Constructions with Mutant BMV Constructions

Standard methods were used with minor modifications (T.

Maniatis et al. (1982) *Molecular Cloning*, Cold Spring Harbor Laboratory, Cold Spring Harbor, N.Y.). To join noncomplementary ends of fragments produced by different restriction endonucleases, 3' protruding ends were trimmed to bluntness with T4 DNA polymerase, and 3' recessed ends were extended to bluntness with either the large fragment of E. coli DNA polymerase I or T4 DNA polymerase.

pB3IC4: E. coli RZ1032 (dut, ung) (T. Kunkel (1985) Proc. Nat. Acad. Sci. USA 82:488) was transformed with pB3TP8 and dUTP-containing ssDNA was isolated after superinfection with M13K07. This DNA was used as a template for oligonucleotide-directed mutagenesis (Kunkel, 1985) to delete 17 of the 18 residues of the pB3TP8 intercistronic oligo(A) tract, and the product clones were screened by dideoxynucleotide sequencing (M. Biggen et al. (1983) Proc. Nat. Acad. Sci. USA 80:3963). The mutagenic oligonucleotide used was d(GACATA-GATCTAATAATAAC). A single A residue from the oligo(A) was retained to preserve the BglII site at the 5' boundary of the core promoter. pB3IC4 is the plasmid which lacks the oligo(A) tract in the subgenomic promoter region.

pB3SG5, 5R, 9, 10, 11, 13, 14, 15, 21, 22: Copies of the AvaI- SacI fragment of pB3TP7 were inserted as duplications in the indicated sites of the RNA3 cDNA region of pB3TP7: pB3SG5: XbaI; pB3SG7: ClaI; pB3SG9: ClaI, XbaI; pB3SG10: XbaI,StuI; pB3SG13: ClaI, XbaI, StuI; pB3SG14: NsiI, XbaI, StuI. Restriction analysis was used to select those insertions with the same orientation as the surrounding cDNA. Multiple rounds of cloning were required to construct those derivatives with multiple insertions of the subgenomic promoter fragment. In the cases of multiple promoter constructions, the use of the AvaI-SacI fragment rather than the smaller AvaI-SalI fragment allowed the distinction of the resulting subgenomic RNA species differentiable in size by gel electrophoresis.

pB3SG5R contains the AvaI-SaCI fragment in the reverse orientation at the XbaI site of pB3TP7.

pB3SG11 contains the AvaI-SalI fragment as a duplication at the XbaI site of pB3TP7. Similarly, pB3SG15, pB3SG21, and p322 contain the BglII-SalI, BsXI-SalI, and DdeI-SalI fragments, respectively.

pB3SG6, 6R: pB3BB1 is a pB3TP7 derivative in which a deletion from base 1168 to the downstream SacI site has been introduced (R. A. French and P. Ahlquist), (1987) J. Virol. 61:1457). The AvaI-SacI fragment of pB3TP8 was introduced into the XbaI site of pB3BB1 in the same orientation as the surrounding cDNA to create pB3SG6, and in the reverse orientation to create pB3SG6R.

pB3IC2, 3, 5, 6: In separate constructions, a BamHI linker (CGCGGATCCGCG, New England Biolabs) was inserted in the AvaI and BglII sites of pB3M1 after filling out the recessed ends with the Klenow DNA polymerase. The small PstI-BamHI fragment of each of these plasmids was ligated with the large PstI-BamHI fragment of pB3BC1 (French and Ahlquist, 1987) to yield intermediate plasmids with the cDNA duplications of pB3IC2 and pB3IC3 respectively. The small PstI-ClaI fragment of each plasmid was then exchanged for the small PstI-ClaI fragment of pB3TP8 (to substitute a bacteriophage T7 promoter for the E- coli promoter for in vitro transcription) to yield pB3IC2 and pB3IC3. In two additional constructions the large EcoRI-HincII fragment of pB3HS1 (French and Ahlquist, 1987) was ligated with the small AvaI-EcoRI fragment of pB3TP8 or pB3IC4. The large BglII-EcoRI fragments of the resultant plasmids were ligated individually with the small BamHI-EcoRI fragment of pB3BC1 to yield pB3IC5 and pB3IC6, respectively.

EXAMPLE 2

In Vitro Transcription, Protoplast Inoculations and RNA Analysis

This example describes the techniques used to examine the functionality of BMV wild-type or altered subgenomic promoter sequences.

Barley protoplasts were isolated as described (L. Loesch-Fries and T. Hall (1980) J. Gen. Virol. 47:323). In vitro transcription in the presence of m7GpppG or GpppG, protoplast inoculation and incubation, viral RNA extraction and analysis and densitometry of the resulting autoradiographs were carried out as described (French and Ahlquist, 1987). Each plasmid construction was tested in at least three independent experiments. Probes for the (+) strand RNA were a 32P-labelled SP6 transcript from subclone pB3HE1, which contains the 200 base HindIII-EcoRI fragment of 3' terminal RNA3 cDNA sequences from pB3TP8, or in certain experiments (FIG. 6 of MS) a similar in vitro transcript complementary to the BglII-SacII region of RNA3. Denaturing gel electrophoresis for negative strand RNA analysis was carried out on formaldehyde genes (Maniatis et al., 1982). Probes for the negative strand RNAs were in vitro transcripts from subclones covering the AvaI-SacI region of BMV RNA3.

Primer extension experiments were carried out after inoculation of 106 protoplasts with transcripts of RNA1 and RNA2 cDNA clones (pB1TP3 and pB2TP5) and transcripts of the appropriate RNA3 cDNA clone. After incubation for 24 h under continuous light, total nucleic acids were isolated and dissolved in 15 µl ddH2O. 1.5 µl of this nucleic acid was mixed with 1 ng of 5'-32P labelled d(GCGAGTCATCT-TACC) (complementary to bases 28–42 of BMV RNA4) in a total volume of 4 µl with 1.5 units of reverse transcriptase (Life Sciences, Inc.) deoxynucleotides at 25 µM each, and final concentrations of 25 mM Tris-Cl pH 8.3, 5 mM $MgCl_2$, 25 mM KCl, and 5 mM DTT. After incubation for 30 min. at 37 C., the products were denatured at 95 C. for 3 min. in an equal volume of 90% formamide, 20 mM EDTA, 0.1% xylene cyanol, 0.1% bromphenol blue, and 3 µl aliquots were electrophoresed on a 12% polyacrylamide, 8.3M urea gel. Marker lanes were prepared similarly except that each reaction contained 50 µM of a single deoxynucleotide, and the template was ssDNA prepared from phage particles isolated after superinfection of pB3SG6-transformed E. coli with helper phage M13K07. Sequence comparisons were made with the assistance of software from the University of Wisconsin Genetics Computer Group.

EXAMPLE 3

Construction of pB3-SGP and Gene Expression

This example describes the construction of a cDNA RNA3 derivative which directs the expression of chloramphenicol acetyl transferase (CAT) activity under the transcription control of the BMV subgenomic promoter, wherein the expression of the subgenomic promoter-CAT gene complex is from a novel site on the RNA3 molecule.

The subgenomic promoter-CAT gene complex is cloned as a AvaI-PstI fragment of pB3CA42 (R. French et al. (1986) Science 231:1294). After filling out the single-stranded ends with Klenow DNA polymerase, this fragment is cloned into the XbaI site of pB3TP7 after similar treatment to create flush ends; the resultant plasmid in which the orientation of the subgenomic promoter-CAT gene complex is the same as in the surrounding cDNA is called pB3-SGP.

RNA transcripts are introduced into barley protoplasts as described in Example 2. CAT gene activity is measured as described in French et al., 1986.

EXAMPLE 4

Construction of pBMVSGP and Two-Stage Gene Expression Controlled by the BMV Subgenomic Promoter This example describes the construction of a recombinant DNA molecule containing the subgenomic promoter of BMV and the bacterial chloramphenicol acetyltransferase (CAT) gene, such that expression of the CAT gene is under the regulatory control of the subgenomic promoter. This molecule can be used to reduce the BMV subgenomic promoter-dependent CAT gene into plant tissue by any means known to the art. Treatment of the genetically modified plant tissue by treating with BMV genomic RNAs to supply RNA- dependent RNA polymerase activity then turns on the expression of the CAT gene under the control of the subgenomic promoter.

The AvaI-PstI fragment of pB3CA42 (R. French et al. (1986) Science 231:1294) provides the subgenomic promoter-CAT gene combination. After repairing all single-stranded overhangs with Klenow DNA polymerase, this fragment is inserted at the BamHI site of pGA355+26 (G. An et al. (1986) Mol. Gen. Genet. 203:245). Restriction endonuclease digests are performed to choose the product in which that the PstI-end is adjacent to the nos promoter, a polII promoter; this recombinant is pBMVSGP. Thus, a primary transcript directed by the nos promoter will be a (–) strand with respect to the subgenomic promoter and the CAT coding region. There is no translation initiation site in the nos-derived portion of the primary transcript.

pBMVSGP is introduced into tobacco protoplasts using the technique of electroporation (M. Fromm et al. (1985) Proc. Natl. Acad. Sci. 82:5824). Primary (–) strand transcripts will be constitutively synthesized by cellular RNA polymerase II.

Subgenomic promoter-dependent expression of CAT is accomplished by introducing BMV RNAs as the source of RNA-dependent RNA polymerase activity into the genetically modified tobacco protoplasts, as described by L. Loesch-Fries et al. (1985) Virology 143:626. CAT enzymatic activity is measured as described (French et al. (1986)).

We claim:

1. An artificially constructed recombinant DNA molecule comprising the nucleotide sequence of a (+) strand plant RNA virus subgenomic core promoter selected from the group consisting of tobamoviruses, tobraviruses, bromoviruses, cucumoviruses and alfalfa mosaic virus, wherein said (+) strand RNA virus comprises a consensus sequence selected from the group consisting of AUCUAUGUU and sequences having a single mismatch thereto, and wherein said (+) strand RNA virus further comprises an activating domain corresponding to the nucleotide sequence from a BstXI site to a BglII site of the cDNA corresponding to the RNA of FIG. 2, and wherein said activating domain is positioned 5' to said subgenomic core promoter sequence.

2. The recombinant DNA molecule of claim 1 wherein said subgenomic core promoter is the subgenomic promoter of brome mosaic virus.

3. A recombinant DNA molecule comprising the subgenomic promoter of claim 2 and further comprising a plant-expressible gene under the regulatory control of said subgenomic promoter.

4. The recombinant DNA molecule of claim 2 wherein said subgenomic promoter comprises the core promoter sequence from a BglII site to a SalII site of the cDNA corresponding to the RNA of FIG. 2, and further comprises the activating sequence from a BstXI site to a BglII site of the cDNA corresponding to the RNA of FIG. 2, wherein said activating domain is located no more than 95 nucleotides upstream of a subgenomic transcription start site.

5. The recombinant DNA molecule of claim 2 wherein said subgenomic promoter comprises the core promoter sequence from a BglII site to a SalI site of the cDNA corresponding to the RNA of FIG. 2, and farther comprises the activating sequence from an AvaI site to a BglII site of the cDNA corresponding to the RNA of FIG. 2, wherein said activating domain is located no more than 95 nucleotides upstream of a subgenomic transcription start site.

6. The recombinant DNA molecule of claim 2 further comprising a second copy of said subgenomic core promoter and a second copy of said activating domain, wherein said second copy of said activating domain is positioned 5' to said second copy of a subgenomic core promoter to form a second subgenomic promoter and wherein said second subgenomic promoter is positioned within said artificially constructed recombinant DNA molecule to allow functioning of said second subgenomic promoter within an RNA copy of said recombinant DNA molecule.

7. An artificially constructed recombinant DNA molecule comprising a subgenomic promoter, wherein said subgenomic promoter comprises a nucleotide sequence from brome mosaic virus from a BstXI site to a SalI site of the cDNA corresponding to the RNA of FIG. 2, and duplicate copies of an activating domain of brome mosaic virus, wherein said duplicate sequence is from an AvaI site to a BglII site of the cDNA corresponding to the RNA of FIG. 2, wherein said duplicate activating domain sequence is located about 220 nucleotides upstream of a subgenomic transcription start site, said subgenomic promoter further comprising a consensus sequence selected from the group consisting of AUCUAUGUU and sequences having a single mismatch thereto, and said recombinant DNA molecule further comprising a plant-expressible gene under the regulatory control of said subgenomic promoter.

* * * * *

UNITED STATES PATENT AND TRADEMARK OFFICE
CERTIFICATE OF CORRECTION

PATENT NO. : 5,466,788
DATED : November 14, 1995
INVENTOR(S) : Paul G. Ahlquist and Roy C. French It is certified that error appears in the above-indentified patent and that said Letters Patent is hereby corrected as shown below:

Column 2, line 26: "ha (+) strand" should read --a (+) strand--
Column 5, line 49: delete "subsequent figures"
Column 6, line 12: "and 15." should read --and 15 are presented in this figure.--
Column 6, line 14: "RNA3are" should read --RNA3 are--
Column 7, line 60: "polynerase" should read --polymerase--
Column 16, line 31: "Springer-Verlaz Berlin Glover (ed.)" should read
--Springer-Verlag, Berlin; Glover (ed.)
Column 17, line 43: "R.A. French" should read --R. French--
Column 18, line 20: "(FIG. 6 of MS)" should read --(e.g., for Figure 6)
Column 18, line 28: "106" should read --$10^6$--
Column 20, line 24: "farther" should read --further--.
Column 20, line 46: "Bg11I" should read --Bg1II--

Signed and Sealed this

Thirtieth Day of April, 1996

*Attest:*

BRUCE LEHMAN

*Attesting Officer*   Commissioner of Patents and Trademarks